United States Patent [19]

Dyott

[11] Patent Number: 4,818,071
[45] Date of Patent: Apr. 4, 1989

[54] FIBER OPTIC DOPPLER ANEMOMETER

[75] Inventor: Richard B. Dyott, Orland Park, Ill.

[73] Assignee: Andrew Corporation, Orland Park, Ill.

[21] Appl. No.: 716,340

[22] Filed: Mar. 26, 1985

[51] Int. Cl.$^4$ ................................................ G01P 3/36
[52] U.S. Cl. .................................. 356/28.5; 356/337; 356/349
[58] Field of Search ...................... 356/28.5, 349–350, 356/320, 337; 350/96.15, 96.3

[56] References Cited

U.S. PATENT DOCUMENTS

| | | | |
|---|---|---|---|
| 4,154,529 | 5/1979 | Dyott | 356/28.5 |
| 4,255,048 | 3/1981 | Franke | 356/28.5 |
| 4,307,938 | 12/1981 | Dyott | 350/96.3 |
| 4,493,528 | 1/1985 | Shaw et al. | 350/96.15 |
| 4,552,456 | 11/1985 | Endo | 356/28.5 X |
| 4,557,551 | 12/1985 | Dyott | 350/96.15 |
| 4,564,262 | 1/1986 | Shaw | 350/320 |
| 4,569,588 | 2/1986 | Nishiwaki et al. | 356/28.5 |
| 4,575,238 | 3/1986 | Knühtsen et al. | 356/28.5 |
| 4,589,725 | 5/1986 | Dyott | 350/96.16 |
| 4,589,728 | 5/1986 | Dyott et al. | 350/96.15 X |
| 4,637,716 | 1/1987 | Auweter et al. | 356/28.5 |

FOREIGN PATENT DOCUMENTS 0107021 5/1984 European Pat. Off. .

OTHER PUBLICATIONS

Dyott, "The Fibre-optic Doppler Anemometer", *Microwaves, Optics and Acoustics*, Jan. 1978, vol. 2, No. 1, pp. 13–18.

H. Auweter and D. Horn, "Fiber-Optical Quasi-Elastic Light Scattering of Concentrated Dispersions"; Journal of Colloid and Interface Science, (vol. 105, No. 2; 6/85, pp. 399–409).

Tanaka, "Measurement of the Velocity of Blood Flow (in vivo) Using a Fiber Optic Catheter and Optical Mixing Spectroscopy"; Applied Optics, (vol. 14, No. 1; 1/75; pp. 189–196).

Ross et al, "Determination of the Mean and Standard Deviation . . . of Submicron Particles Using FODA"; *Journal of Colloid and Interface Science*, (vol. 64, No. 3; 5/78; pp. 533–542).

R. Graf, *Dictionary of Electronics*, pp. 278–279, (Sams and Co., 1974).

Primary Examiner—Stephen C. Buczinski
Assistant Examiner—Bernarr Earl Gregory
Attorney, Agent, or Firm—Stephen G. Rudisill

[57] ABSTRACT

A fiber optic doppler anemometer comprises a source of coherent light, a directional coupler formed by the combination of a pair of single-mode optical fibers, and a photoelectric transducer. The first end of the first fiber receives an incident beam of light from the source and guides it through the directional coupler to the second end of the first fiber, which is located adjacent to a body of moving particles to be measured, where both the second end of the first fiber and the moving particles reflect a portion of the incident light back into the first fiber. The reflected light, which has a frequency different from that of the incident beam entering the first fiber, is directed back through the directional coupler which couples a portion of the reflected light toward the first end of the second fiber. The photoelectric transducer receives the light emerging at the first end of the second fiber and converts it into analogous electrical signals.

This system may be used as a velocimeter using the Doppler effect to measure the velocity of moving particles and to measure the sizes of particles with Brownian motion.

10 Claims, 2 Drawing Sheets

FIBER OPTIC DOPPLER ANEMOMETER

FIELD OF THE INVENTION

The present invention relates generally to the field of fiber optics and, more particularly, relates to its application to various measurements, including size and velocity, of particles in liquids or gases.

This invention is especially applicable to laser Doppler anemometers in which an optical fiber is used to transmit light to and from the measurement zone.

DESCRIPTION OF THE PRIOR ART

Anemometers, which use the Doppler shift principle to measure the velocity of particles in liquids or gases, are well known. Generally, a beam of coherent light from a laser is used to illuminate the moving particles. A difference frequency signal, which is directly proportional to the velocity of the particle, is then obtained by mixing the reflected or scattered light, which is Doppler-shifted in frequency, with the incident light in a photo-detector. One of the problems associated with such a system is that some provision is required for getting the light to and from the scattering particles. This may be difficult if, for instance, the measuring zone is in an opaque liquid or gas.

An alternative approach is to use an optical fiber to handle the transmission of light. This method was first reported by Tanaka and Benedek, (Tanaka, T., and Benedek, G. B.: "Measurement of the Velocity of Blood Flow (in vivo) Using a Fibre Optic Catheter and Optical Spectroscopy", Appl. Opt., 1975, vol. 14, pp. 189-196) as a means of measuring blood flow in vivo. But their experimental setup has the major disadvantage that 75% of the light to the photo detector is lost in a half silvered mirror which acts as a beam splitter.

A much improved Doppler anemometry system is described in Dyott U.S. Pat. No. 4,154,529 entitled "System For Detecting Reflected Laser Beams". This system, in place of the silvered mirror mentioned above, uses an aperture in a mirror inclined at an angle of 45° to the beam axis, through which a beam of polarised light from a HeNe laser is focused onto the end of an optical fiber. At the far end of the fiber, the reflected and scattered light from the particles re-enters the fiber at the full numerical aperture, and the resulting light emerging from the near end of the fiber is converted to a relatively large-diameter parallel beam by a launching lens. Although a small fraction of the beam is lost through the aperture in the mirror, most of it is reflected to be focused by a second lens onto the photo detector. This system provides significant improvement in efficiency, but, as is apparent, requires an elaborate arrangement involving the apertured mirror, launching as well as detecting lenses, and a complex mechanism for aligning these components perfectly.

The system of the present invention eliminates the above mentioned problems and constitutes a significant improvement in fiber-optic anemometry.

SUMMARY OF THE INVENTION

It is a principal object of this invention to achieve a high degree of simplicity in an anemometer which uses the Doppler shift principle to measure the velocity and size of particles in liquids or gases.

Another specific object of the invention is to provide improved efficiency and accuracy in an anemometer that uses the Doppler effect on a reflected light beam to measure the velocity of moving particles.

It is a further object of the invention to provide a more efficient system for measuring the sizes of particles with Brownian motion by analyzing the frequency spectrum of light scattered from such particles.

A still further object of the invention is to provide a system of the foregoing type which can perform measurements in otherwise inaccessible situations.

Yet another object of the invention is to provide all the above advantages in a system which is portable and, therefore, usable in field situations where data may be recorded for further laboratory analysis.

Other objects and advantages of the invention will be apparent from the following detailed description and the accompanying drawings.

BRIEF DESCRIPTION OF THE DRAWINGS

For the purpose of facilitating an understanding of the invention, the accompanying drawings illustrate a preferred embodiment.

FIG. 5 is a graph of Log $S(\omega)$ versus Log f, as applicable to the measurement of particle size using the system of FIG. 1.

DESCRIPTION OF THE INVENTION

Although the invention will be described in connection with the preferred embodiment, it is to be understood that there is no intention to limit the invention to this particular embodiment; various changes and modifications can be made therein without departing from the spirit and scope of the invention, and it is intended to cover all such changes and modifications that fall within the spirit and scope of the appended claims.

Figure 1:
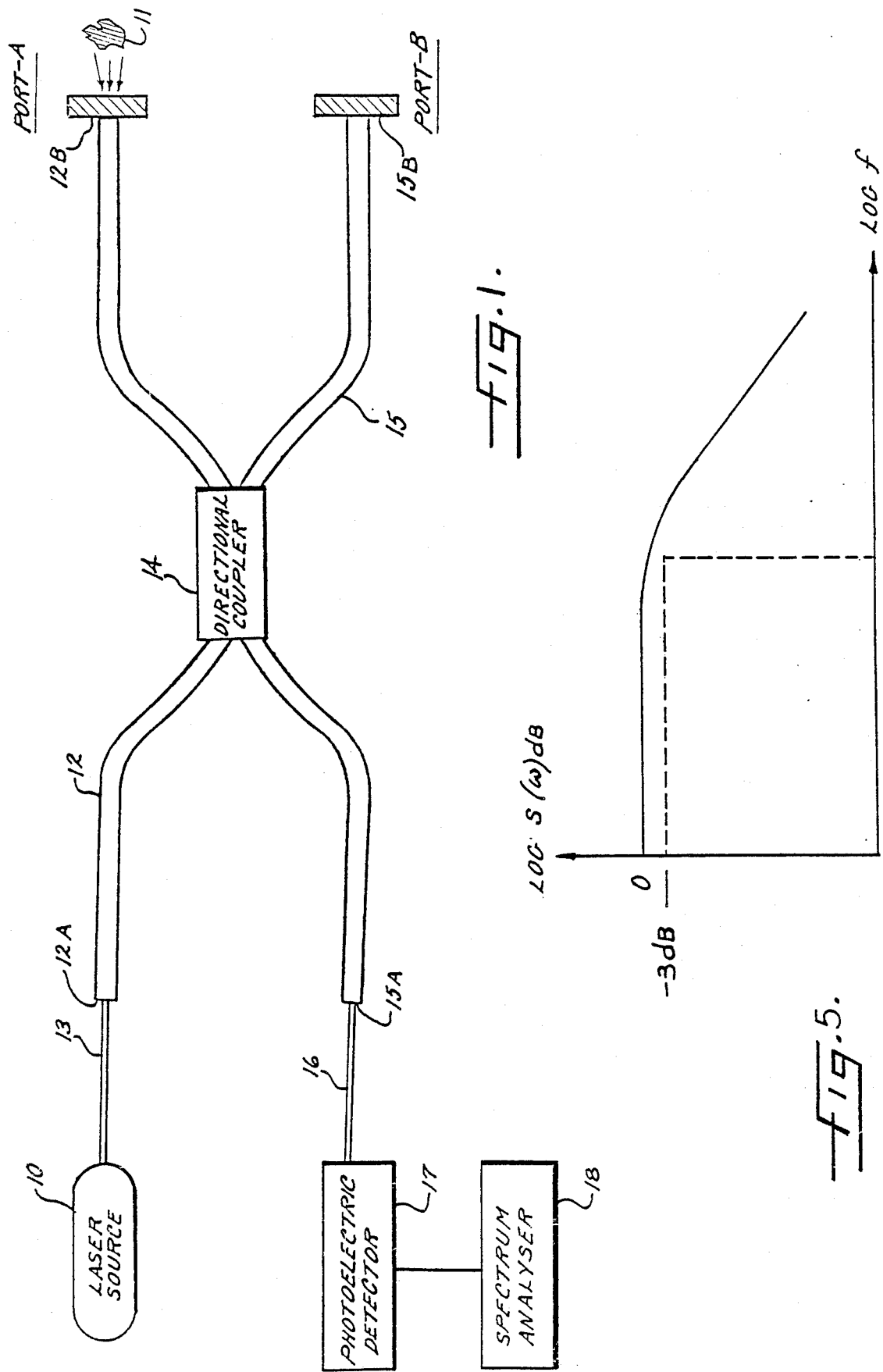
FIG. 1 is a schematic diagram of an optical fiber system embodying the invention and suitable for use as a Doppler anemometer.

Referring now to FIG. 1, a fiber optic anemometer uses a laser beam source 10, i.e., a source of coherent light, to determine the velocity and/or size of particles 11 located adjacent to the end 12B of an optical fiber 12. The basic principle on which the system of FIG. 1 operates, involves the measurement of velocities by directing a coherent beam of light from the laser source 10 onto the moving particles 11 and detecting the frequency change, between the incident laser beam and the reflected beam, due to the Doppler effect; this effect is a direct function of the velocity of the particles reflecting the light. Measurement of particle sizes is accomplished by directing the coherent light beam onto the particles under test and detecting the frequency change between the incident and reflected beams due to the Brownian motion of the particles, which is a function of their size. These techniques have been used previously to measure the velocity and size of particles, but not with the increased simplicity of design and operation provided by the present invention.

Still referring to FIG. 1, the laser beam source 10 generates an incident monochromatic laser beam 13 which is projected into a first end 12A of the optical fiber 12. The incident beam, while being transmitted through the fiber 12, passes through a directional coupler 14, which divides the beam into two components on the basis of a predetermined splitting ratio; one of these components passes through the remainder of the fiber 12 to emerge at a port A located at the far end 12B of the fiber 12, while the other component passes through a second fiber 15 to emerge at a port B. A more detailed description of the kind of fibers used and the actual coupling mechanism will be given below.

Port A of the system is placed in the field of the medium under test, and hence a portion of the incident beam emerging at the far end 12B of the fiber 12 is reflected off the moving particles 11 under investigation. A Doppler shift in the frequency of this incident beam is caused by motion of the particles 11 in any direction other than at right angles to the beam. More specifically, the frequency increases if the motion of the particles is toward the fiber, and the frequency decreases if the motion of the particles is away from the fiber.

The beam reflected from the particles 11 enters the far end 12B of the fiber 12, and propagates through it without interruption until it encounters the directional coupler 14 which, as mentioned before, divides the beam into two portions on the basis of a predetermined ratio. Beyond the coupler 14 a portion of the reflected beam is transmitted back toward the laser source 10 through the fiber 12 to emerge at its near end 12A. The intensity of this emerging reflected beam is generally insufficient to upset the source of the laser beam.

The other portion of the reflected beam coming out of the directional coupler 14 is transmitted through the the second fiber 15 to emerge at its near end 15A. This portion of the reflected beam 16 is projected onto a photo-electric detector 17.

It will be understood that a difference in refractive indices exists at port A between the material of the fiber 12 and that of the surrounding medium in which port A is located. Because of this mismatch, the static end 12B of the fiber 12 reflects a portion of the incident beam back into the end 12B of the first fiber. This reflected beam in turn is transmitted along the fiber 12 without interruptions until it passes through the directional coupler 14, where, as in the previous cases, it is divided into two portions. One portion of the reflected beam passes through the remainder of the fiber 12 to emerge at its near end 12A and is again insufficient to upset the source of the laser beam. The other portion of this reflected beam is transmitted through the remainder of the fiber 15 to emerge at its near end 15a.

Thus, at the input of the photoelectric detector 17 there exists a combination of two light signals generated because of separate reflections from (i) the particles facing port A and (ii) the mismatch existing at port A. The photo-electric detector 17 mixes these two signals, i.e., the light reflected from the particles 11 and the light reflected from the static far end 12B of the fiber and transduces them into an electrical signal whose frequency can be used to determine the velocity of the particles 11. More specifically, the component of the light reflected at port A due to the mismatch and emerging at the near end 15A of the first fiber is used as a reference signal for beating against the Doppler-shifted signal reflected from the particles 11 at port A. Since the reference signal comes only from the static far end 12B of the first fiber, where light is reflected to some extent because of the small change in refractive index between the fiber end and the surrounding medium, no secondary beat signals are generated, leading to minimal distortion in the measurement of the frequency change.

In the system of FIG. 1, the detected signals from the photodetector 17 are fed into a spectrum analyser 18. For measurements covering a range of frequencies, such as is generated by Brownian motion, a summation of the signal over a period of time is an advantage, and a spectrum analyzer of the integrating type may be used. For signals which are more coherent, as in the measurement of vibrational or linear velocities, a standard spectrum analyzer is sufficient.

Reverting now to the path of the originally incident beam 13 after it passes through the directional coupler 14, a portion of this beam emerges through the far end 15B of the fiber 15 at port B which is placed in a medium of matching refractive index which absorbs almost all of the energy incident upon it. The refractive index of this medium should be matched as closely as possible to that of the fiber because a difference in refractive indices at port B can give rise to noise from spurious reflections which will adversely affect the accuracy of measurement.

It is an important aspect of this invention to have at least a slight difference in refractive indices between the fiber and the surrounding medium at port A, in order to ensure a reference signal, while maintaining this difference as close to zero as possible at port B, to prevent spurious reflections.

In the measurement of particle velocities, the shift in frequency due to the Doppler effect, between the incident beam and the beam reflected or scattered back from the particles under test, is first determined as explained above. The velocity of the particles can then be calculated from the relationship existing between the frequency shift, the particle velocity V, the wavelength λ of light in the propagating medium and the angle of radiation of the fiber.

Another application for the system of this invention is measurement of the diameter of particles suspended in a liquid. It is well known that particles with Brownian motion give a characteristic Lorentzian frequency spectrum. The frequency spectrum of the intensity of the scattered light, and hence the current signal as detected by the photoelectric detector is given by:

$$S(\omega_d) \alpha \frac{\Gamma(\theta)}{[\omega_d^2 + \Gamma^2(\theta)]} \quad (1)$$

where $\omega_d$=Doppler radian frequency. Since the mode of detection in this case is homodyne:

$$\Gamma(\theta) = D \left\{ \frac{4\pi n_o}{\lambda_o} \sin \frac{\theta^2}{2} \right\} \quad (2)$$

where
$n_o$=refractive index of the liquid
$\lambda_o$=free space wavelength
$\theta$=scattering angle.

D is the diffusion constant for particles in Brownian motion and is related to the particle radius a, the temperature T and viscosity $\eta$ of the liquid by the Stokes-Einstein relation as follows:

$$D = \frac{kT}{6\pi\eta a} \quad (3)$$

where k=Boltzmann's constant.

FIG. 5 shows the curve resulting from a plot of Log $S(\omega_d)$ against Log $\omega_d$ or Log f, by using the Log f and dB scales on a spectrum analyser. As indicated, at the half power point or −3 dB point:

$$\omega_d{}^2 = \tau^2(\theta) \quad (4)$$

Thus the radian frequencies $\omega_d$ may now be expressed as:

$$\omega_d = D\left\{\frac{4\pi n_o}{\lambda_o}\sin(90°)\right\}^2 \quad (5)$$

Since $\omega_d$ is a known factor from the analysis, this equation (5) can be solved to obtain the value of D, which can then be substituted in equation (1) to obtain a solution for the value of the particle radius a.

In equation (5) $\theta/2$ is taken to be 90° although the fiber will accept angles $(\theta/2)\pm\psi$ where $\psi$ is a function of the refractive index of the liquid and the angle of radiation of the fiber. Hence, for strict accuracy an average should be taken over the angle of acceptance, but the correction factor $\sin\psi/\psi$ will be very close to unity for the low angles of radiation used in the system of this invention.

Optical fibers used in previous fiber-optic anemometric systems have been multi-mode fibers, mainly because the relatively large core diameters involved accept a relatively large quantum of reflected light from the particles under investigation. These particles are often extremely small, such as fine silica granules which are typically 50-100 nm in size, and the portion of light which is reflected off the particles back toward the fiber is relatively small. Multi-mode fibers permit a relatively large portion of this reflected light back into the fiber, but this is done at the expense of a deterioration of the signal due to the presence of modal noise. See, for example, "The Phenomenon of Modal Noise" in *Analogue and Digital Optical Fiber Systems*, R. E. Epworth, Proc. 4th European Conf. in Optical Communications, September 1978, Genoa, Italy.

Single mode fibers, as used in the system of this invention, admit a smaller portion of the reflected light back into the fiber because of the smaller core diameters. However, it has now been found that even with the smaller core diameters, single mode fibers have sufficient light transfer characteristics to provide accurate measurements in anemometric systems of the type presented in the illustrative case. Even though the quantity of light transferred is reduced, it has been found that single-mode fibers provide better discrimination in fiber-optic anenometers because of the higher signal-to-noise ratio.

Further, the use of multi-mode fibers in previous fiber-optic anenometers has entailed the use of directional couplers which function at a relatively low level of efficiency, primarily due to the existence of differential mode coupling, i.e., most of the power coupled from the primary fiber comes from high order modes and is transferred into higher order modes in the secondary fiber. A second difficulty is that evanescent coupling in multi-mode fibers is very weak unless the cladding thickness is significantly reduced by polishing or preferential etching.

By using single mode fibers, the present invention reduces the severity of these problems. It will be understood that, although the preferred embodiment of the invention utilizes special D-shaped birefringent fibers to provide ease of alignment at either end of the fibers and a simpler design of the directional coupler, other types of single-mode fibers and directional couplers may be used, as long as a ready reference to the plane of polarization is available.

In the illustrative embodiment of the present invention, the two fibers 12 and 15 in the system described above and as represented by FIG. 1, are single-mode birefringent D-shaped optical fibers. Single-mode fibers as well as birefringent D fibers, have a variety of advantages on their own and when applied together, as exemplified in this invention by the use of optical fibers that are single-moded bi-refringent and D-shaped, bring about a high degree of improvement in interferometric sensor systems.

In general, optical fibers in transducer systems offer the advantages of low signal attenuation, flexibility, reasonable information-transfer capacity and a mode of transmission that does not generate interference and is unaffected by external interference. Single-mode fibers, in particular, by limiting wave propagation through the fiber to a single mode, increase sensitivity by eliminating modal noise. This offsets the problem of the smaller quantity of light reflected by the test particles back into the fiber caused by the necessarily small cores of single-mode fibers.

Single-mode propagation also has the advantage of providing well defined patterns for coupling the fiber to optical devices. Furthermore, a single constant phase velocity is necessary in fiber-optic sensor applications requiring comparison of the phase of the sensed signal to that of a reference signal.

The coupling coefficient of a single-mode directional coupler is sensitive to the state of polarization of the light in the fiber. Thus the use of a polarized source together with a polarization-preserving fiber and a polarization-holding directional coupler eliminates the noise caused by a randomly polarized source acting upon the sensitivity of the coupling coefficient to the state of polarization. Polarization-maintaining fibers guarantee that the polarization of the signal is fixed in a definite or constant angular relationship with respect to the fiber core. It is here that the properties of the D fiber are directly applicable. By using an elliptical core and a D-shaped outer surface, the D fiber provides a ready reference to the plane of polarization and hence permits precise alignment of a fiber with a second fiber of the same shape, or with a polarization-sensitive optical device. This property contributes directly to a simplified design for the directional coupler.

Figure 2:
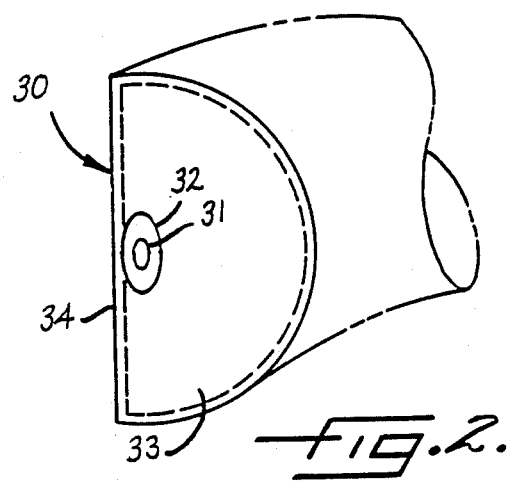
FIG. 2 is an end view of a preferred optical fiber for use in the system of FIG. 1.

FIG. 2 illustrates a typical embodiment of a D fiber 30 which has an elliptical core 31 surrounded by a cladding 32 with an index of refraction lower that that of the core. The dimensions and refractive indices of the core 31 and its cladding 32 are selected such as to provide a single mode guiding region. Being elliptical, this guiding region maintains the polarization of optical signals propagating through it in alignment with either axis of the ellipse. Thus, the major and minor axes of the elliptical cross-section represent two transverse orthogonal axes permitting the de-coupling of waves polarized along these axes. A support layer 33 surrounds the guiding region and provides added mechanical strength and flexibility. Its optical properties are not critical except for the fact that the refractive index is higher than that of the cladding 32 to prevent light being trapped within the cladding.

The guiding region of the fiber as defined by the core 31 and cladding 32 can be located sufficiently close to the surface to permit coupling to a guided wave. This is accomplished by removing a thin portion of the support layer 33 and also a portion of the cladding 32 (e.g., by etching to the dashed contour in FIG. 2) if necessary to achieve the desired degree of coupling.

The outer surface of the optical fiber as defined by the support layer 33 in FIG. 2 has a D-shaped cross section, with the flat surface 34 of the D extending parallel to the major axis of the elliptical guiding region on the side of the fiber closest to the guiding region. This D-shaped outer surface of the optical fiber permits the axes of the elliptical core 31 to be precisely aligned with a second fiber of the same shape, or with a polarization-sensitive optical device, by using the flat surface 34 of the D as an indexing or reference surface. More precisely, in the system illustrated in FIG. 1 the shape of the D fiber allows a ready reference to the sense of polarization at the laser beam end as well as the photodetector end.

Figure 3:
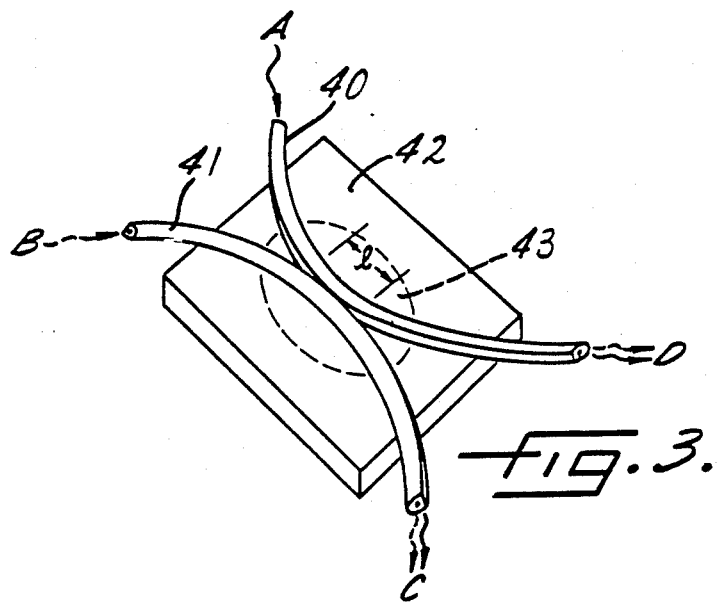
FIG. 3 is a perspective view of a fiber optic directional coupler suitable for use with this invention and utilizing the optical fiber of FIG. 2.

FIG. 3 represents a preferred fiber-optic directional coupler for use in the system of this invention. It is comprised of two D-fibers 40, 41, of the type shown in FIG. 2, positioned adjacent each other on a flat substrate 42. The flat surfaces of the fibers 40, 41 contact each other along etched lengths l, and their guiding regions are aligned to permit the gradual exchange of energy between the guiding regions along the length l of the fibers, as defined by the region 43. As shown in FIG. 3, the D fibers 40, 41 are curved rather than straight in their unstressed configuration, in such a way that the flats of the D's are located on the convex surfaces of the curved fibers. This facilitates the alignment of the guiding regions of the two optical fibers.

Figure 4:
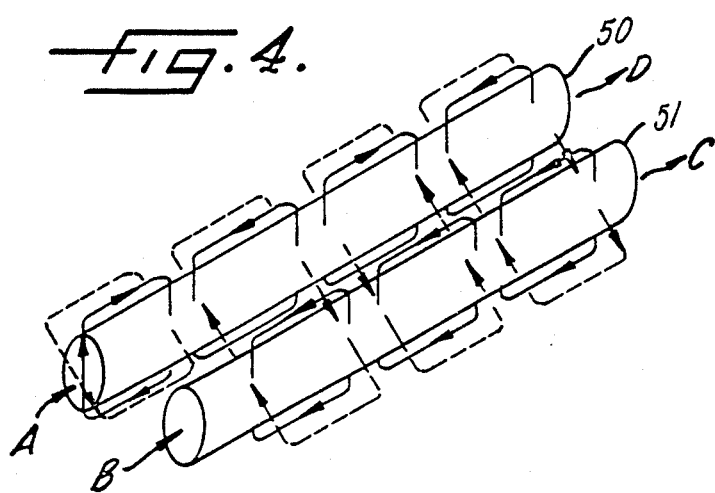
FIG. 4 is a schematic perspective view of the active area of the directional coupler of FIG. 3, showing the exchange of electromagnetic energy between the two fibers forming the coupler.

The schematic diagram of FIG. 4 illustrates the operation of the directional coupler of FIG. 3. Coupling is accomplished in terms of an exchange or transfer of the electromagnetic fields E, H propagating down the cores 50, 51 of the respective fibers 40, 41. A portion of the electromagnetic field energy in the incident signal A is gradually transferred from one core 50 to the other core 51. In general, the relative amount of energy from signal A that is transferred from one core 50 to the other core 51, i.e. the "splitting ratio", is proportional to the amount of coupling per unit length and the length l over which the coupling occurs. Hence the splitting ratio required for any particular application is a factor controlled by the degree of proximity of the cores 50, 51 of the two optical fibers 40, 41 forming the directional coupler. It is apparent here that the design and construction of the directional coupler of FIG. 3 is simplified by the use of the D-shaped optical fibers as represented by FIG. 2 because of the ease with which the 2 fibers may be precisely aligned within the area of coupling. The smaller separation between the cores possible because of the flat external surfaces, results in a high degree of coupling between the two optical fibers.

I claim as my invention:

1. A fiber optic Doppler anemometer comprising a source of coherent light,
   a directional coupler formed by the combination of first and second single-mode optical fibers, each of said fibers having a core and cladding of different refractive indices and forming a single-mode guiding region, with a first end of said first fiber receiving an incident beam of coherent light from said source and guiding said light through said directional coupler to a second end of said first fiber which is located adjacent to a body having a moving surface to be measured, whereby both the second end of said first fiber and said moving surface reflect a portion of said light back into said first fiber, said incident beam and the light reflected from said second end of said first fiber having the same frequency, the portion of said light reflected from said moving surface having a frequency different from that of the incident beam entering said fiber, said reflected light being directed back through said directional coupler, said directional coupler coupling a portion of said reflected light toward a first end of said second fiber, and
   a photoelectric transducer for receiving the portion of said reflected light coupled by said directional coupler into the first end of said second fiber, and converting said light to analogous electrical signals.

2. A fiber optic anemometer as set forth in claim 1 wherein said core of each of said fibers has an elliptical cross-section.

3. A fiber optic anemometer as set forth in claim 2 in which each of said optical fibers has a core having a non-circular cross-section defining two transverse orthogonal axes which, in combination with said different refractive indices, de-couples waves polarized along said axes,
   said guiding region being located sufficiently close to the surface of the fiber along a selected length of the fiber, to allow coupling to a contiguous medium by exposure or expansion of the field of the guiding region,
   the outer surface of each of said fibers having a non-circular cross-section with a predetermined geometric relationship to said guiding region and said orthogonal transverse axes so that the location of said guiding region and the orientation of said axes can be ascertained from the geometry of said outer surface.

4. A fiber optic anemometer as set forth in claim 2 wherein for each of said fibers the portion of said outer surface that is closest to said guiding region is substantially parallel to the major transverse axis of said elliptical cross-section.

5. A fiber optic anemometer as set forth in claim 1 wherein each of said fibers includes a support layer surrounding said guiding region and forming said non-circular outer surface of said fibers.

6. A fiber optic anemometer as set forth in claim 1 wherein the outer surface of each of said fibers has a generally D-shaped cross-section.

7. A fiber optic anemometer as set forth in claim 1 wherein said directional coupler is comprised of said optical fibers fused along selected lengths thereof with said guiding regions aligned with each other, and with the fiber surfaces that are closest to the respective guiding regions facing each other so that at least a portion of a wave propagated through either guided region is coupled into the other guiding region.

8. A fiber optic anemometer as set forth in claim 1 wherein said source of coherent light is a source of polarized light, said first and second fibers are polarization-maintaining fibers, and said directional coupler is polarization-maintaining.

9. A fiber optic anemometer as set forth in claim 1 wherein the second end of said second fiber is coupled to a medium having a refractice index that substantially matches the refractive index of said second fiber.

10. A fiber optic Doppler anemometer comprising a source of coherent light,
   a directional coupler formed by the combination of first and second single-mode optical fibers, each of said fibers having a single core and cladding of different refractive indices and forming a single-mode guiding region,
   each of said fibers having a core with a noncircular cross-section defining two transverse orthogonal axes which, in combination with said different refractive indices, decouple waves polarized along said axes,
   said guiding region being offset from the geometric center of the fiber and located sufficiently close to the one side of the fiber to allow coupling to a guided wave through said one side by expansion of the field of the guiding region,
   the outer surface of each of said fibers having a noncircular cross-section forming an indexing surface with a predetermined geometric relationship to said guiding region and said orthogonal transverse axes so that the location of said guiding region and the orientation of said axes can be ascertained from the geometry of said indexing surface on the exterior of the fiber,
   a first end of said first fiber receiving an incident beam of coherent light from said source and guiding said light through said directional coupler to a second end of said first fiber which is located adjacent to a body of moving particles to be measured, whereby both the second end of said first fiber and said moving particles reflect a portion of said light back into said first fiber, said incident beam and the light reflected from said second end of said first fiber having the same frequency, the portion of said light reflected from said moving particles having a frequency different from that of the incident beam entering said fiber, said reflected light being directed back through said directional coupler, said directional coupler coupling a portion of said reflected light toward a first end of said second fiber, and
   a photoelectric transducer for receiving the portion of said reflected light coupled by said directional coupler into the first end of said second fiber, and converting said light to analogous electrical signals.

* * * * *